US 9,018,351 B2

(12) United States Patent
Jeong et al.

(10) Patent No.: US 9,018,351 B2
(45) Date of Patent: Apr. 28, 2015

(54) PEPTIDE APTAMERS AGAINST TENASCIN C

(71) Applicant: Industry-Academy Cooperation Foundation, Yongin-si (KR)

(72) Inventors: Sun Joo Jeong, Seoul (KR); Mee Young Kim, Seoul (KR); Ok Ran Kim, Seoul (KR); Heui Ran Lee, Seongnam-si (KR); Kee Rang Park, Cheongju-si (KR)

(73) Assignee: Industry-Academy Cooperation Foundation, Dankook University, Yongin-Si, Gyeonggi-Do (KR)

( * ) Notice: Subject to any disclaimer, the term of this patent is extended or adjusted under 35 U.S.C. 154(b) by 0 days.

(21) Appl. No.: 13/955,537

(22) Filed: Jul. 31, 2013

(65) Prior Publication Data
US 2014/0030736 A1 Jan. 30, 2014

Related U.S. Application Data

(62) Division of application No. 12/675,665, filed as application No. PCT/KR2008/004911 on Aug. 22, 2008.

(30) Foreign Application Priority Data

Aug. 28, 2007 (KR) .................. 10-2007-0086538

(51) Int. Cl.
*C07K 7/08* (2006.01)
*C07K 7/06* (2006.01)
*G01N 33/574* (2006.01)

(52) U.S. Cl.
CPC ............ *G01N 33/57492* (2013.01); *C07K 7/08* (2013.01); *G01N 2800/00* (2013.01)

(58) Field of Classification Search
CPC . C07K 7/08; G01N 2800/00; G01N 33/57492
See application file for complete search history.

(56) References Cited

FOREIGN PATENT DOCUMENTS

| KR | 10-2009-0021751 A | 3/2009 |
| WO | WO-92/07872 A1 | 5/1992 |
| WO | WO-02/096941 A2 | 12/2002 |
| WO | WO-2009/028838 A1 | 3/2009 |

OTHER PUBLICATIONS

Orend et al., Potential oncogenis action of tenascin-C in tumorigenesis, The International Journal of Biochemistry & Cell Biology, vol. 37:1066-1083 (2005).*
Pas et. al., Analysis of structure and function of tenascin-C, The International Journal of Biochemistry & Cell Biology, vol. 38:1594-1602 (2006).*
Jones et al., Tenascin-C in development and disease: gene regulation and cell function, Matrix Biology, vol. 19:581-596 (2000).*
(Continued)

*Primary Examiner* — Christina Bradley
*Assistant Examiner* — Randall L Beane
(74) *Attorney, Agent, or Firm* — Clark & Elbing LLP

(57) ABSTRACT

The present invention relates to an anti-tenascin C peptide aptamer having a specific amino acid sequence and a diagnosis kit comprising it. The anti-tenascin C peptide aptamer of the instant invention shows a predominant clearance rate due to its small molecular weight as well as specific binding affinity to tenascin C, having excellent advantages in in vivo or ex vivo tumor imaging.

5 Claims, 10 Drawing Sheets

(56) References Cited

OTHER PUBLICATIONS

Jarvinen et al., Mechanical loading regulates the expression of tenascin-C in the myotendinous junction and tendon but does not induce de novo synthesis in the skeletal muscle, Journal of Cell Science, vol. 116:857-866 (2003).*

Daniels et al., "A tenascin-C aptamer identified by tumor cell SELEX: Systematic evolution of ligands by exponential enrichment," Proc Natl Acad Sci USA. 100(26):15416-15421 (2003).

Hicke et al., "Tenascin-C aptamers are generated using tumor cells and purified protein," J Biol Chem. 276(52):48644-48654 (2001).

Hicke et al., "Tumor targeting by an aptamer," J Nucl Med. 47(4):668-678 (2006).

Ireson et al., "Discovery and development of anticancer aptamers," Mol Cancer Ther. 5(12):2957-2962 (2006).

International Search Report for International Application No. PCT/KR2008/004911, mailed Oct. 30, 2008 (3 pages).

Orend et al., "Tenascin-C induced signaling in cancer," Cancer Lett. 244(2):143-63 (2006).

* cited by examiner

Adenocarcinoma

Squamous cell carcinoma

Bronchioloalveolar carcinoma

Normal tissue

SEQUENCE LISTING

```
<160> NUMBER OF SEQ ID NOS: 27

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct

<400> SEQUENCE: 1

Phe His Lys Pro Phe Phe Pro Lys Gly Ser Ala Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct

<400> SEQUENCE: 2

Phe His Lys His Lys Ser Pro Ala Leu Ser Pro Val
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Phe His Lys His Ser Pro Arg Ser Pro Ile Phe Ile
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Construct
```

```
<400> SEQUENCE: 4

Phe His Lys His Gln Trp Pro Pro Arg Gly Leu Ser
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Construct

<400> SEQUENCE: 5

Trp His Lys His Pro Ser Ser Tyr Pro Gln Val Phe
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Construct

<400> SEQUENCE: 6

Leu His Lys His Arg Pro Thr Ile Thr Leu Pro Lys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Construct

<400> SEQUENCE: 7

Thr His Lys His Phe Pro Lys His Met Pro Arg Gln
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic Construct

<400> SEQUENCE: 8

Phe His Lys Pro Phe Lys Pro Thr His Arg Thr Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic Construct

<400> SEQUENCE: 9

Phe His Lys Thr Pro Arg Ile Ala Pro Pro Pro Leu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic Construct

<400> SEQUENCE: 10
```

Trp His Lys Ile Pro Gln Lys Ala Pro Leu Asn Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Construct

<400> SEQUENCE: 11

Phe His Lys Pro Pro Lys Ser Ala Pro Pro Ser Ala
1               5                   10

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
ggtacagtgg gacagcaggt g                                                  21

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct

<400> SEQUENCE: 13
aactggattg agtgttcgtg g                                                  21

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
ccctgctctg gaagacacc                                                     19

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
ataaggcgta gcagccttga                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
tgacatcaag aaggtggtga                                                    20

<210> SEQ ID NO 17

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
tccaccaccc tgttgctgta                                                    20

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct

<400> SEQUENCE: 18
ataggatccg aacaagcccc t                                                  21

<210> SEQ ID NO 19
<211> LENGTH: 21
<212> TYPE: DNA
<213> ORGANISM: Artificial Sequence
<220> FEATURE:
<223> OTHER INFORMATION: Synthetic Construct

<400> SEQUENCE: 19
gccggatccc tatgttgttg c                                                  21

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
ccctcatagt tagcgtaacg                                                    20

<210> SEQ ID NO 21
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 21

Phe His Lys Pro Phe Xaa Pro Lys Xaa Ser Ala Xaa
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 22

Phe His Lys His Xaa Xaa Pro Xaa Xaa Xaa Pro Xaa
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 23

Phe His Lys Pro Xaa Xaa Pro Xaa Xaa Ser Pro Xaa
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 24

Phe His Lys His Xaa Xaa Pro Xaa Xaa Ser Ala Xaa
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Synthetic Construct

<400> SEQUENCE: 25

Val Ser Pro Lys Ser His Leu Lys Ala His Pro Phe Gly Gly Gly
1               5                   10                  15
```

```
<210> SEQ ID NO 26
<211> LENGTH: 15
<212> TYPE: PRT
<213> ORGANISM: Artificial Sequence
<220> FEATURE:
<223> OTHER INFORMATION: Synthetic Construct

<400> SEQUENCE: 26

Phe His Lys Pro Phe Phe Pro Lys Gly Ser Ala Arg Gly Gly Gly
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic Construct

<400> SEQUENCE: 27

Phe His Lys His Lys Ser Pro Ala Leu Ser Pro Val Gly Gly Gly
1               5                   10                  15
```

PEPTIDE APTAMERS AGAINST TENASCIN C

CROSS-REFERENCE TO RELATED APPLICATIONS

This application is a divisional of U.S. patent application Ser. No. 12/675,665, filed Feb. 26, 2010, which is the U.S. national stage filing under 35 U.S.C. §371 of PCT International Application No. PCT/KR2008/004911, filed Aug. 22, 2008, which claims priority from Korean Patent Application No. 10-2007-0086538, filed Aug. 28, 2007.

BACKGROUND OF THE INVENTION

1. Field of the Invention

The present invention relates to an anti-tenascin C peptide aptamer and its uses.

2. Background of Technique

In addition to genetic mutations in cancer cells themselves, tumorigenesis is also accompanied by changes in the surrounding stroma and extracellular matrix (ECM). Interactions between tumor and stromal cells contribute to tumor formation and progression, but the ECM proteins involved remain to be identified. Tenascin C is an adhesion modulatory ECM protein that is expressed during development, but not in normal adult tissues (1, 2). It is mostly found in tumor-specific microenvironments and its high level expression appears to play a role in tumor formation and progression (3, 4).

Tenascin proteins (C, X, R and W) are large glycoproteins that form multimeric complexes and may contribute to pathological states in which tissue remodeling processes are involved (1, 2, 4). For example, it is likely that tenascin C stimulates diverse signaling pathways leading to cell proliferation, invasion and tumor formation (5).

The prominent expression of tenascin C in many solid tumors provides an outstanding diagnostic and therapeutic target for tumor site detection and treatment in vivo. Especially, a large isoform of tenascin C is generated by alternative splicing of mRNA and its protein expression has been shown to be associated with tumor progression (6-8). Since tenascin C is a potential biomarker for the diagnosis and prognosis of many cancers (9), anti-tenascin C antibodies are effective in tumor targeting and a radiolabeled monoclonal antibody is in clinical trial (10-12). In addition, RNA aptamers have also been generated to be used as targeting and imaging tools (13, 14).

Throughout this application, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THE INVENTION

The present inventors have made intensive studies to develop a novel aptamer to specifically bind to tenascin C for inhibiting biological functions of tenascin C as well as targeting tenascin C in vivo or ex vivo. As results, we have discovered that the present aptamer obtained by a phage display technology possessed an enhanced specificity in binding to tenascin C.

Accordingly, it is an object of this invention to provide an anti-tenascin C peptide aptamer.

It is another object of this invention to provide a diagnosis kit for detecting a tumor, which comprises the peptide aptamer.

Other objects and advantages of the present invention will become apparent from the following detailed description together with the appended claims and drawings.

In one aspect of the present invention, there is provided an anti-tenascin C peptide aptamer represented by the following Formula 1:

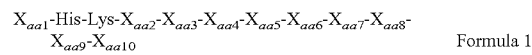
$$X_{aa1}\text{-His-Lys-}X_{aa2}\text{-}X_{aa3}\text{-}X_{aa4}\text{-}X_{aa5}\text{-}X_{aa6}\text{-}X_{aa7}\text{-}X_{aa8}\text{-}X_{aa9}\text{-}X_{aa10}$$  Formula 1 wherein $X_{aa1}$ represents Phe, Trp, Leu or Thr, and $X_{aa2}$ represents Pro, His, Thr or Ile, and $X_{aa3}$ represents any amino acid selected from 20 amino acids, and $X_{aa4}$ represents Phe, Ser, Pro, Trp, Lys, Arg or Gln, and $X_{aa5}$ represents Pro, Arg, Ser, Thr, Lys or Ile, and $X_{aa6}$ represents any amino acid selected from 20 amino acids, and $X_{aa7}$, represents any amino acid selected from 20 amino acids, and $X_{aa8}$ represents any amino acid selected from 20 amino acids, and $X_{aa9}$ represents Arg, Pro, Phe, Leu, Val, Thr, Asn or Ser, and $X_{aa10}$ represents any amino acid selected from 20 amino acids.

The present inventors have made intensive studies to develop a novel aptamer to specifically bind to tenascin C for inhibiting biological functions of tenascin C as well as targeting tenascin C in vivo or ex vivo. As results, we have discovered that the present aptamer obtained by a phage display technology possessed an enhanced specificity in binding to tenascin C.

As an alternative to antibody- and RNA aptamer-based tenascin C targeting, peptide aptamers can be used to selectively bind tenascin C-expressing cancer cells and solid tumors. As a tumor targeting tool, tenascin C-binding peptide aptamers can be applied to gene therapeutic tools such as liposomes, viral vectors and nanoparticles (19-21). Since tenascin C modulates the cell adhesion and remodels surrounding tissues to promote tumor progression, tenascin C-binding peptide might also has a great potential to block tenascin C induced tumor cell formation and progression.

The present invention provides a peptide aptamer which specifically binds to tenascin C.

The term "aptamer" used herein with reference to tenascin C means a peptide with binding affinity to tenascin C, comprising 4-40, preferably 5-30, more preferably 5-20 and most preferably 8-15 amino acid residues. The peptide aptamer may is in a linear or circular form.

The aptamer of the instant invention is represented by the Formula 1. As described in Formula 1, some positions in the peptide may be occupied by any amino acids, i.e., any of 20 amino acids. The 20 amino acids include Gly, Ala, Val, Leu, Ile, Phe, Pro, Glu, Asp, Gln, Asn, His, Arg, Lys, Ser, Thr, Trp, Cys, Met and Tyr.

According to a preferred embodiment, $X_{aa1}$ in the Formula 1 represents Phe. Preferably, $X_{aa2}$ represents Pro or His.

According to a preferred embodiment, $X_{aa3}$ represents Phe, Lys, Ser, Gln, Pro or Arg. Preferably, $X_{aa4}$ represents Ser or positive-charged amino adds (e.g., Arg or Lys) and more preferably Ser.

According to a preferred embodiment, $X_{aa5}$ represents Pro. Preferably, $X_{aa6}$ represents Lys, Ala, Ser, Pro, Tyr, Ile, His or Thr.

Preferably, $X_{aa7}$ in the Formula 1 represents Gly, Leu, Pro, Arg, Thr, Met or His. According to a preferred embodiment, $X_{aa8}$ represents Ser, Ile, Gly, Gln, Leu, Pro or Arg.

According to a preferred embodiment, $X_{aa9}$ represents Pro. Preferably, $X_{aa10}$ represents Arg, Val, Ile, Ser, Phe, Lys, Gln, Leu, Pro or Ala.

The illustrative amino acid sequences of the instant peptide aptamers are described in SEQ ID NOs: 1-11 and preferably SEQ ID NO: 1 or NO: 2.

The aptamer of this invention has a peptide structure. The term "peptide" as used herein means a linear or circular, preferably circular molecule formed by linkage between amino acid residues via peptide bond. The peptide of the present invention may be prepared by chemical synthesis method, particularly solid-phase synthesis techniques (Merrifield, *J. Amer. Chem. Soc.*, 85:2149-54(1963); Stewart, et al., *Solid Phase Peptide Synthesis*, 2nd. ed., Pierce Chem. Co.: Rockford, 111(1984)) known in the art.

Even though the present peptide aptamers exhibit excellent stability in itself, their stability may be enhanced by modification of amino acid residues of peptides. According to a preferred embodiment, the stability of the peptide aptamers is increased by modification at any amino acid residue, preferably the N-terminal with Gly residue(s), acetyl group, fluorenyl methoxy carbonyl group, formyl group, palmitoyl group, myristyl group, stearyl group or polyethylene glycol (PEG), and most preferably Gly residue(s).

Where Gly residue(s) is further bound to the N-terminal of the peptide aptamer, the number of the Gly residue is in a range of 1-8, preferably 2-6, more preferably 2-4 and most preferably 3.

The peptide aptamer against tenascin C may be used in diagnosis and treatment of cancer, atherosclerosis and psoriasis. The peptide aptamer may be rapidly cleared from bloodstream due to its very small molecular weight as compared with antibodies. The rapid blood clearance rate is very important to in vivo diagnosis imaging because its concentration within the blood is a pivotal factor causing the background in imaging. In addition, the rapid blood clearance rate is also significantly critical in therapeutic applications because its concentration within the blood is a main cause generating the toxicity.

Accordingly, it could be appreciated that the present anti-tenascin C peptide aptamer has a plausible advantage in tumor treatment, and in vivo or ex vivo diagnosis imaging.

In another aspect of the present invention, there is provided a diagnosis kit for detecting a tumor, which comprises the peptide aptamer described above.

The anti-tenascin C peptide aptamer used in this invention detects effectively tumors by specific binding to tenascin C present in tumor cells, particularly in the nucleus of tumor cells.

For enhancing the utility of the peptide aptamer as a diagnosis agent, a substance (e.g., dye) generating a detectable signal may be bound to the aptamer by directly or indirectly labeling. A signal-generating substance bound to aptamer includes, but not limited to, radio-isotope (e.g., $C^{14}$, $I^{125}$, $P^{32}$ and $S^{35}$), chemical (e.g., biotin), fluorescent [fluoresin, FITC (fluoresein Isothiocyanate), rhodamine 6G, rhodamine B, TAMRA (6-carboxy-tetramethyl-rhodamine), Cy-3, Cy-5, Texas Red, Alexa Fluor, DAPI (4,6-diamidino-2-phenylindole) and Coumarin], luminescent, chemiluminescent and FRET (fluorescence resonance energy transfer) substances. Various methods for labels and labelings are described in Ed Harlow and David Lane, *Using Antibodies: A Laboratory Manual*, Cold Spring Harbor Laboratory Press, 1999.

The above-mentioned labels may be directly or indirectly bound to the peptide aptamer. For example, the peptide aptamer may be indirectly labeled by labeling where the biotin is bound to the peptide aptamer and then the label-conjugated streptavidin (or avidin) is fused with the biotin.

In in vitro or ex vivo detecting tumors using the peptide aptamer, tumors may be detected using a biosample isolated from body. In this instance, a diagnosis kit of the present invention may be usually used according to conventional immunoassay protocols. The immunoassay may be carried out by various quantitative or qualitative immunoassay protocols well known to one of skill in the art. The immunoassay formats include, but not limited to, radioimmunoassay, radio-immunoprecipitation, immunoprecipitation, ELISA (enzyme-linked immunosorbent assay), capture-ELISA, inhibition or competition assay, sandwich assay, flow cytometry, immunofluorescent staining or immunoaffinity purification. The methods of the immunoassay or immunostaining are described in *Enzyme Immunoassay*, E. T. Maggio, ed., CRC Press, Boca Raton, Fla., 1980; Gaastra, W., *Enzyme-linked immunosorbent assay (ELISA)*, in Methods in Molecular Biology, Vol. 1, Walker, J. M. ed., Humana Press, NJ, 1984; and Ed Harlow and David Lane, *Using Antibodies: A Laboratory Manual*, Cold Spring Harbor Laboratory Press, 1999, which are incorporated herein by reference.

In in vivo detection of tumors using the peptide aptamer, tumors are detected by a direct injection of the peptide aptamer into body.

Cancers or tumors detected by this invention are not particularly limited, and preferably include stomach cancer, lung cancer, breast cancer, ovarian cancer, liver cancer, bronchogenic cancer, nasopharyngeal cancer, laryngeal cancer, pancreatic cancer, bladder cancer, colon cancer, uterine cervical cancer, brain cancer, prostaic cancer, bone cancer, skin cancer, thyroid cancer, parathyroid cancer or ureter cancer, and most preferably glioblastoma, colon adenocarcinoma or lung carcinoma.

The anti-tenascin C peptide aptamer useful in the present invention is peptide aptamer of the present invention described hereinabove, preferably comprising the amino acid sequence of SEQ ID NO: 1 or NO: 2.

The present invention will now be described in further detail by examples. It would be obvious to those skilled in the art that these examples are intended to be more concretely illustrative and the scope of the present invention as set forth in the appended claims is not limited to or by the examples.

BRIEF DESCRIPTION OF THE DRAWINGS

FIG. 1A, Total RNA from cultured human tumor cell lines was analyzed by RT-PCR. fbg; fibrinogen glob, AS; alternative splicing. Glyceraldehyde-3-phosphate dehydrogenase (GAPDH) was shown as a control. FIG. 1B, Whole cell extracts of cultured human tumor cell lines were analyzed by Western blot analysis. Tubulin served as a loading control.

FIG. 6A showed the result that glioblastoma cells were plated on the fibronectin (FN)/tenascin-C (TNC) substratum with #2 peptide and scrambled peptide and observed under microscope. Magnification, ×100. FIG. 6B was the results that numbers of round cell was scored and presented as percentage. Four independent experiments were performed. FIG. 6C represented U118MG migration with #2 peptides or scrambled peptides. The data are representative of three independent experiments. SD, P<0.001 relative to no treated samples. FIG. 6D exhibited that glioblastoma cells were plated on the fibronectin (FN)/tenascin-C (TNC) substratum with #2 peptide or scrambled peptide. Whole cell extract were prepared and with anti-β-catenin antibody. Anti-β-actin was used as control.

EXAMPLES

Experimental Materials and Methods

Cell Culture

Figure 1A:
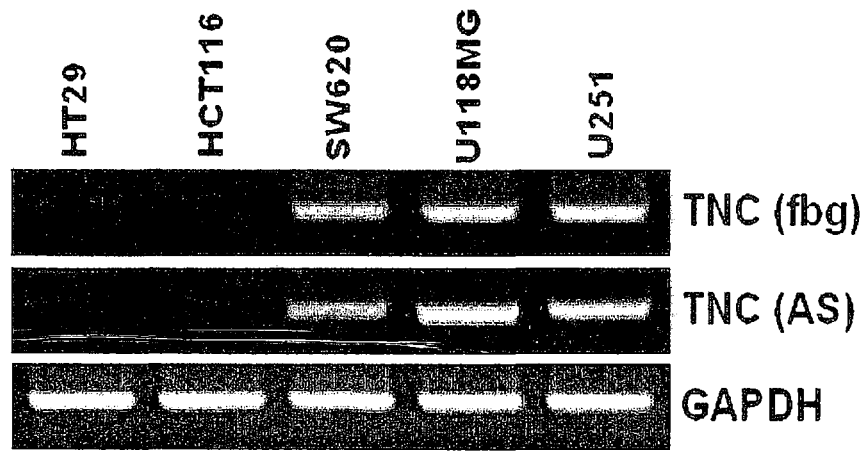
FIGS. 1A-1B represent expression pattern of tenascin C mRNA and protein in cultured human tumor cell lines.

Human U118MG, U251 and T98G glioblastoma cells, HCT116, HT-29, DLD-1, SW480 and SW620 colorectal cancer cells and 293T human embryonic kidney cells (American Type Culture Collection, Rockville, Md.) were cultured in DMEM with 10% fetal bovine serum (FBS).

Reverse Transcription-PCR

Total cellular RNA was isolated with TRIzol (Invitrogen), reverse transcribed with M-MuLV reverse transcriptase, and used in the PCR reactions. The following PCR primers were used: tenascin C fibrinogen glob (TNC fbg), 5'-GGTACAGTGGGACAGCAGGTG-3' (forward; SEQ ID NO:12) and 5'-AACTGGATTGAGTGTTCGTGG-3' (reverse; SEQ ID NO:13); TNC alternative splicing (AS), 5'-CCCTGCTCTGGAAGACACC-3' (forward; SEQ ID NO:14) and 5'-ATAAGGCGTAGCAGCCTTGA-3' (reverse; SEQ ID NO:15); GAPDH, 5'-TGACATCAAGAAGGTGGTGA-3' (forward; SEQ ID NO:16) and 5'-TCCACCACCCTGTTGCTGTA-3' (reverse; SEQ ID NO:17). The cDNA was subjected to standard PCR and the products were analyzed on 2% agarose gel followed by ethidium bromide staining.

Western Blot Analysis

Whole cell extracts (40 μg) were prepared, fractionated by 8% SDS-PAGE, blotted to nitrocellulose membranes, and incubated with anti-tenascin C antibody (BC24; Sigma-aldrich, Saint Louis, Miss.). Anti-α-tubulin was used as control.

Recombinant Proteins

Recombinant (His)$_6$-tagged tenascin C protein was prepared from TNCfnA-D plasmid containing tenascin C alternative splice domain (kindly provided by Dr. Harold P. Erickson, Duke University Medical Center). TNCfnA-D plasmid was amplified with TNCfnA-D sense (5'-ATAGGATCCGAACAAGCCCCT-3'; SEQ ID NO:18) and TNCfnA-D antisense (5'-GCCGGATCCCTATGTTGTTGC-3'; SEQ ID NO:19) primers. The amplified fragment was inserted into the BamHI site of the pET28a+ vector (Novagen) to generate vector (His)$_6$-tagged-TNCfnA-D. The ligated DNA was used to transform E. coli BL21 (DE3) cells, and the recombinant DNA was confirmed by DNA sequence analysis. To prepare (His)$_6$-tagged-TNCfnA-D fusion proteins, transformed bacteria were cultured in LB medium with kanamycin to an optical density of 0.6 at 600 nm. 0.4 mM isopropyl-1-thio-D-galactopyranoside was added and the cultures were further incubated for 4 hrs at 30° C. The cells were collected by centrifugation and resuspended in 15 ml of lysis buffer (50 mM NaH$_2$PO$_4$, 300 mM NaCl, 10 mM imidazole, pH 8.0) with 1 mM phenylmethanesulfonyl fluoride and 1 mg/ml lysozyme and sonicated for 7 min with a 30% pulse. After the lysate was cleared by centrifugation at 13,000 rpm for 30 min at 4° C., the (His)$_6$-tagged-TNCfnA-D fusion protein was purified with Ni-NTA agarose according to the manufacturer's instructions (Qiagen, Valencia, Calif.). Full-length tenascin C protein was purchased from Chemicon (Temecula, Calif.). Fibronectin was purchased from Sigma (St. Louis, Mo.).

Biopanning of Tenascin C-Binding Phages

The phage-display peptide library (Ph.D.-12) was purchased from New England Biolabs (Beverly, Mass.). The phage library was panned for O/N at 4° C. in 96-well plates coated with 0.15 ml (His)$_6$-tagged-TNCfnA-D (10 μg/ml) or full-length tenascin C protein (20 μg/ml) in 0.1 M NaHCO$_3$ (pH 8.6). The wells were then blocked with blocking buffer (0.1 M NaHCO$_3$ [pH 8.6], 0.5% BSA and 0.02% NaN$_3$) for 1 h at 4° C. and 2×10$^{11}$ pfu/ml phages were added to the target protein-coated plates. After incubation for 30 min at 25° C., unbound or weakly bound phages were removed by rinsing ten times with TBST, and bound phages were eluted by incubation for 8 min in 0.1 ml elution buffer (0.2 M glycine-HCl [pH 2.2] and 0.1% BSA). The recovered phages were used to infect E. coli ER2738 (NEB), amplified, purified by precipitation with 1/6 vol PEG/NaCl (20% (w/w) polyethylene glycol 8000 and 2.5 M NaCl) and used in the next round of panning. After three rounds, independent clones were isolated on LB/IPTG/X-gal plates, and phage titers were calculated from the number of plaques formed.

DNA Sequence Analysis

Thirty five clones from the two independent selections were sequenced. Individual phage clones were purified by precipitation with PEG/NaCl. The phage pellets were suspended in iodide buffer (10 mM Tris-HCl [pH 8.0], 1 mM EDTA and 4 M NaI) and single-stranded phage DNA was precipitated with ethanol. The nucleotide sequences of the isolated DNAs were determined with an automatic sequencer (ABI prism) and primer 5'-CCCTCATAGTTAGCGTAACG-3' (SEQ ID NO:20).

Synthesis of Peptides

The selected peptides and a scrambled peptide were synthesized in Peptron Inc. (Republic of Korea). The peptide sequences were FHKPFFPKGSARGGG (#1; SEQ ID NO:26), FHKHKSPALSPVGGG (#2; SEQ ID NO:27) and VSPKSHLKAHPFGGG (#2 scramble; SEQ ID NO:25). All peptides were synthesized with amino-terminal conjugated biotin residues.

Immunocytochemistry

Cells were grown on coverslips, fixed with 3.7% paraformaldehyde for 15 min at room temperature, and permeabilized with 0.5% Triton X-100 in PBS. They were washed and blocked in 10% normal calf serum, 0.5% gelatin in PBS for 30 min at room temperature. Staining was carried out with biotin-labeled peptide for 1 hr at room temperature. Secondary TEXAS RED-conjugated streptavidin (Calbiochem, La Jolla, Calif., 1:200 dilution) was applied at room temperature for 50 min in the dark. The cells were counterstained with Hoechst33258.

Immunofluorescence Assays on Frozen Tissue Sections

A tumor xenograft was established by subcutaneous injection of $2\times10^6$ HT29 or U118MG cells into one flank of nude mice. When the tumor diameter reached approximately 9-10 mm, the mice were killed, and the tumor tissue was obtained and lyophilized for storage at −80° C. Frozen sections 8-10 μm thick were cut, fixed with 3.7% paraformaldehyde for 15 min at room temperature, and permeabilized with 0.5% Triton X-100 in PBS. The cells were washed and blocked with 10% fetal bovine serum, 10% non fat dry milk and 3% BSA in PBS for 2 hrs at room temperature. They were stained with anti-tenascin C antibody (BC24; Sigma-Aldrich, Saint Louis, Miss., 1:1000 dilution), anti-β-catenin antibody (clone 14; BD Transduction Laboratories, Germany, 1:100 dilution), or biotin-labeled peptide for O/N at 4° C. Secondary FITC-conjugated anti-mouse IgG antibody (Sigma-Aldrich, Saint Louis, Miss., 1:1000 dilution) or TEXAS RED-conjugated streptavidin (Calbiochem, La Jolla, Calif., 1:1000 dilution) was used for 1 hr at room temperature in the dark. Cells were counterstained with Hoechst33258.

Immunofluorescence Analysis of Tissue Microarrays

The lung tissue microarray was constructed from archived paraffin blocks at Seoul National University Bundang Hospital. It is composed of 36 adenocarcinomas, 15 squamous cell carcinomas, 1 bronchioloalveolar carcinoma, and 1 normal lung. Sections were dewaxed in xylene and rehydrated in graded concentrations of ethanol and distilled water. For antigen retrieval, sections were heated for 20 min in Target Retrieval Solution, Tris/EDTA (pH 9; Dako) using a pressure cooker. Staining was carried out with anti-tenascin C antibody (BC24; Sigma-aldrich, Saint Louis, Mo., 1:1000 dilution) or biotin-labeled peptide for O/N at 4° C. Secondary anti-mouse FITC-conjugated IgG antibody or TEXAS RED-conjugated streptavidin was used for 1 hr at room temperature in the dark. Cells were counterstained with Hoechst33258.

Adhesion Assay

Microtiter plates (6-well, Nunc, Roskilde, Denmark) were coated with 1 μg/cm² of fibrobectin or fibronectin and tenascin C for overnight at 4° C. The noncoated plastic surface was blocked with 1% heat-inactivated BSA in PBS. Before plating, cells were serum starved for 18 hrs in DMEM and trypsinized. Following soybean trypsin inhibitor treatment (100 μg/ml in PBS), cells were resuspended in serum-free medium and counted by hematocytometer. Approximately $1\times10^5$ cells were plated in each well and the selected peptide aptamer or scramble peptide was treated for 18 hrs, cells were observed under microscope.

Wound Scratch Assay

U118MG cells were grown until they become confluent on a 35 mm dish and were serum starved for 18 hrs in DMEM. A straight line was drawn with a marker on the outer surface of the dish bottom and an artificial wound was made by using a pipet tip. The dish was rinsed and then incubated with the serum free medium in the presence of #2 peptides or #2 scramble peptides. After 18 hrs incubation, cells were counted.

Statistical Analysis

Student's t test was done for most data with Microsoft Excel (Microsoft Corp.)

EXPERIMENTAL RESULTS

Expression of Tenascin C mRNA and Proteins in Human Cancer Cell Lines

Figure 1B:
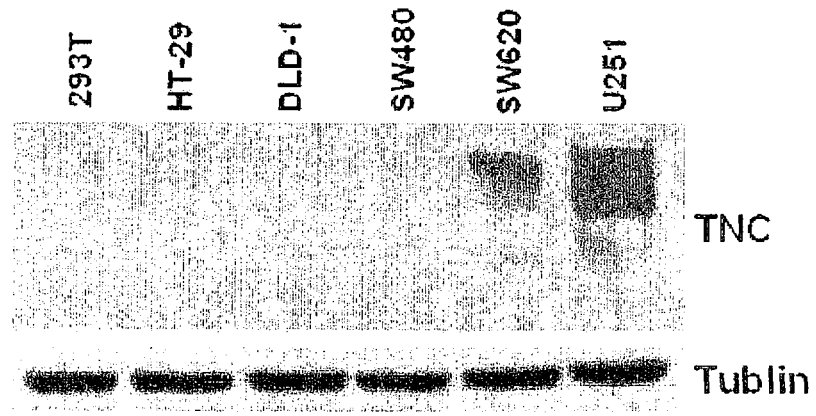

The present inventors first screened for tenascin C expression in diverse human cancer cell lines (U118MG, U251 and T98G glioblastoma cells, HCT116, HT-29, DLD-1, SW480 and SW620 colorectal cancer cells) as well as normal human embryo kidney cells (293T) (FIG. 1). As shown in FIG. 1A, the present inventors observed high levels of tenascin C mRNA in U118MG, U251 and SW620 cells but not in the other cells. Interestingly, two cell lines (U251 and SW620) also expressed the alternatively spliced tenascin C mRNA and high molecular weight tenascin C proteins (FIG. 1B). The present inventors used this information to examine the use of the peptide aptamers to detect tenascin C in cancer cells in the following study.

Identification of Tenascin C Binding Peptide Sequences

Figure 2A:
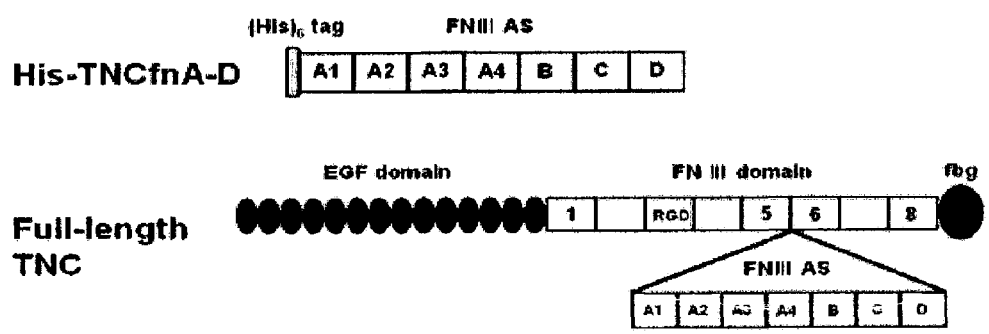
FIG. 2A is a schematic diagram of the recombinant tenascin C proteins used for selecting peptides. FNIII; fibronectin type III, fbg; fibrinogen glob, AS; alternative splicing.

To screen for peptide aptamers that bound to the cancer-specific tenascin C protein isoform, the alternatively spliced domain of fibronectin type III (FN III) (A1-D) was expressed as a His-tagged tenascin C protein (designated His-TNCfnA-D in FIG. 2A). The present inventors also used full-length tenascin C containing the alternatively spliced domains in addition to the EGF domain, fibrinogen glob (fbg) and other constitutively expressed FNIII domains (designated Full-length TNC in FIG. 2A). The present inventors performed three independent selections of peptide aptamers using these two different forms of tenascin C protein as targets.

Figure 2B:
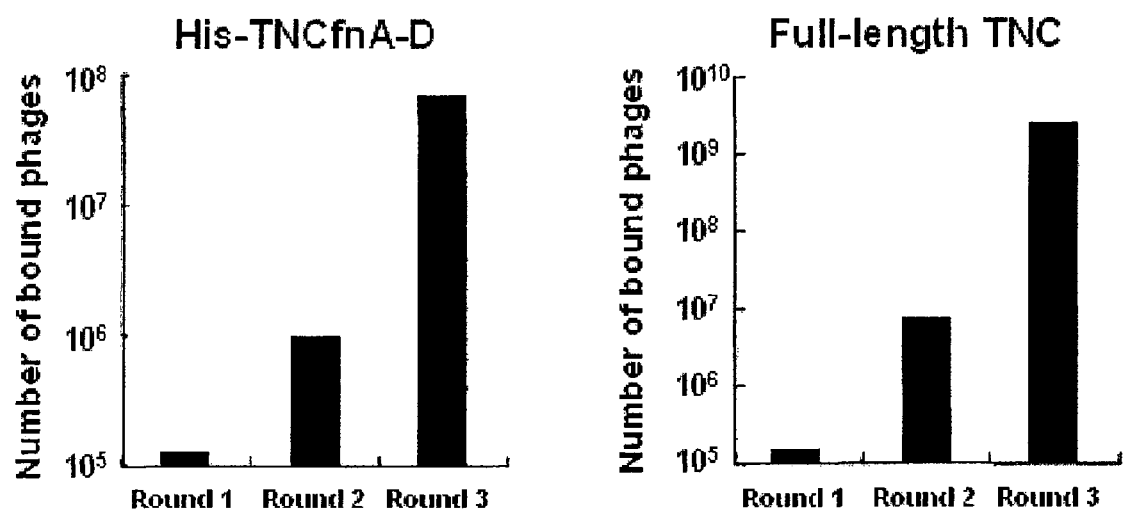
FIG. 2B indicates the number of phages bound after each round of selection for full-length tenascin C.

A significant increase in relative phage yield was obtained after three rounds of biopanning with full-length tenascin C protein (FIG. 2B).

TABLE 1

| Group | Sequences | | Frequency |
|---|---|---|---|
| Group I | F H K P F F P K G S A R | (peptide #1; SEQ ID NO: 1) | 13 |
| | F H K P F - P K - S A - | (consensus; SEQ ID NO: 21) | |
| Group II | F H K H K S P A L S P V | (peptide #2; SEQ ID NO: 2) | 19 |
| | F H K H - - P - - - P - | (consensus; SEQ ID NO: 22) | |
| | F H K P - - P - - S P - | (SEQ ID NO: 23) | |
| | H          A | (SEQ ID NO: 24) | |
| Group III | Non consensus | | 3 |
| | Total clones | | 35 |

Of the 35 clones from the Ph.D.-12 library, thirteen had identical sequences (designated #1), and nineteen others were also identical (designated #2) while the remainder had similar sequences. The consensus sequences (FHK(P/H)-P-S(P/A)-; SEQ ID NOs:23 and 24), found in the majority of the selected peptides, was noted in 35 clones (Table 1). Most sequences contained amino terminal FHKH and SP or $PX_{2-4}P$ motifs. When the present inventors searched for homologous amino acid sequences using BLAST and CDD (Conserved Domain Database, 22), significant homology was found for sequence #1 to the evolutionarily conserved domains of glycosyl hydraloses. Moreover, the #2 sequence also had some homology to glycosylation enzymes as well as glycosyl hydrolases. Since these two peptide sequences were representative of the selected sequences, we synthesized peptide aptamers #1 (FHKPFFPKGSAR; SEQ ID NO:1) and #2 (FHKHKSPALSPV; SEQ ID NO:2), with flanking sequences (-GGG) from M13 coat protein. As a control, the present inventors also synthesized the scrambled form of peptide #2 (VSPKSHLKAHPFGGG; SEQ ID NO:25).

Staining of Human Cancer Cell Lines with the Selected Peptide Aptamers

Figure 3A:
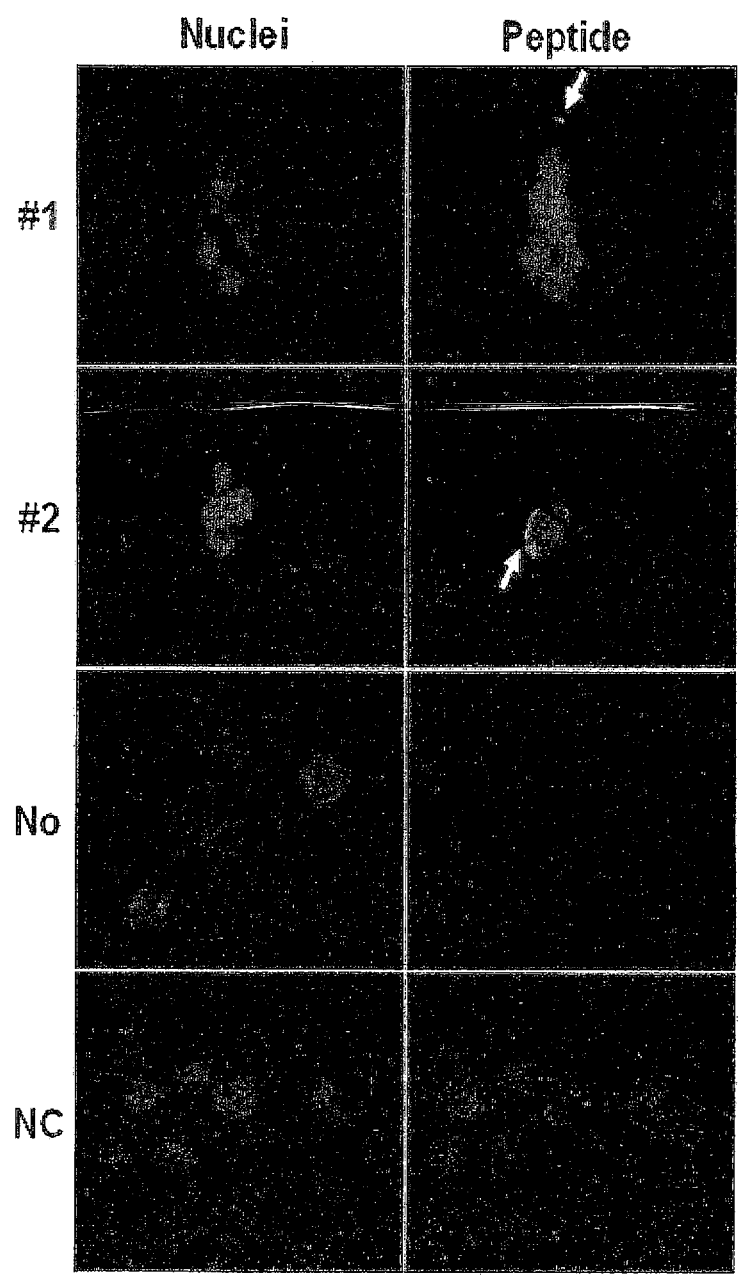
FIGS. 3A-3C represent binding pattern of the selected peptides to cultured cells. Cultured cells of SW620 (FIG. 3A), U251 (FIG. 3B) and HCT116 (FIG. 3C) were incubated at room temperature for 1 hr with 1 mM of biotin-labeled peptide aptamers (#1, #2), control peptide (NC), or peptide aptamer #2 (1 mM) plus anti-tenascin C antibody (1:1000 dilution). Nuclei were counterstained with Hoechst33258. Arrows indicate examples of positively stained cells. Magnification, ×1000 (FIG. 3A and FIG. 3C), ×630 (FIG. 3B).
Figure 3B:
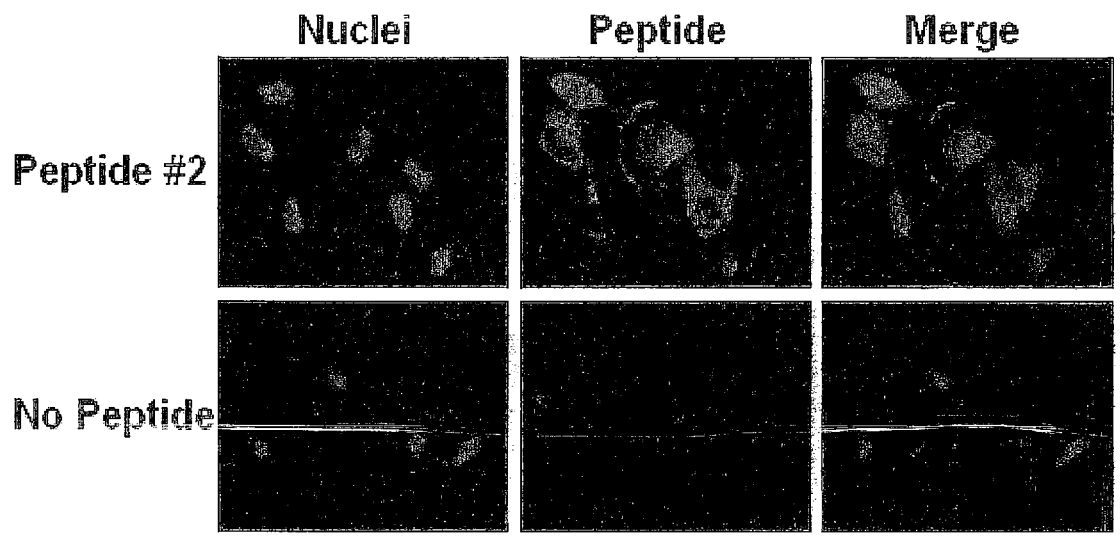
Figure 3C:
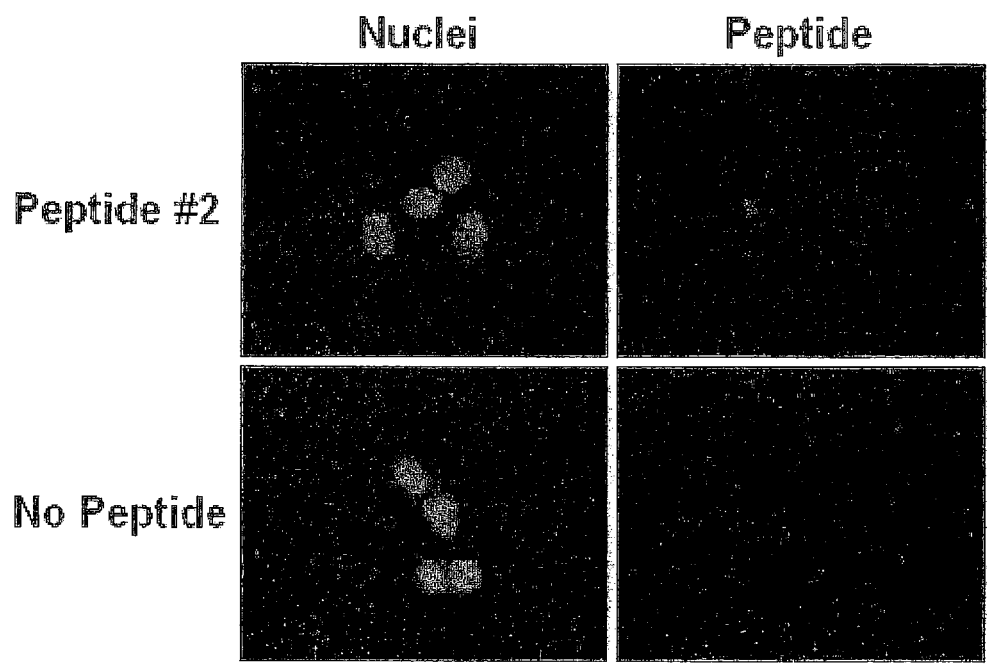

The present inventors utilized U251, SW620 and HCT116 cells as model cell lines for high, medium and no expression of tenascin C protein, respectively (FIG. 1). The biotin-labeled peptide aptamers were used to test whether they recognized the endogenously expressed tenascin C in the cultured cell lines. Interestingly, aptamers #1 and #2 yielded a characteristic staining pattern of spots or long streaks in a polarized region of the plasma membrane of SW620 cells (FIG. 3A). There was no signal with the negative peptide or when aptamer was omitted. Since the peptide aptamer #2 have high frequency and observed a higher level of staining, we used it in subsequent work. The level of staining with U251 cells was higher than with SW620 cells, which may reflect a higher level of tenascin C expression. Interestingly, aptamer #2 stained two distinct areas of the U251 cells: one appeared as a long streak along the plasma membrane and the other was diffuse staining of the cytoplasm (FIG. 3B). When the present inventors stained HCT116 cells that do not express tenascin C protein with aptamer #2, no signal was detected (FIG. 3C). These results demonstrate that aptamer #2 binds to tenascin C protein in the plasma membrane of cancer cells in which expression of tenascin C is high.

Recognition of Tenascin C by Peptide Aptamer #2 in Xenograft Mouse Models

Figure 4A:
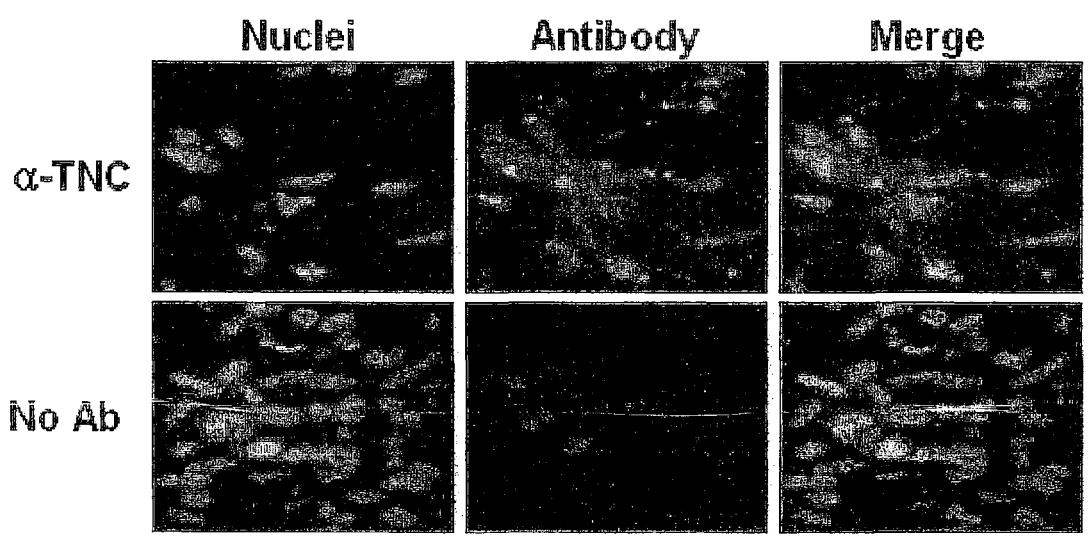
FIGS. 4A-4C represent immunofluorescence detection for binding of #2 peptide aptamer to U118MG-derived tumor xenograft tissue. Frozen tissue sections were incubated at 4° C. for O/N with anti-tenascin C antibody (1:1000 dilution) (FIG. 4A), anti-β-catenin antibody (1:100 dilution) (FIG. 4B), 10 μM biotin-labeled peptide aptamer (#2) or scrambled peptide (#2 scr) (FIG. 4C). Tissues were counterstained with Hoechst33258. Arrows indicate examples of positively stained cells. Magnification, ×630. Results using a xenograft mouse model with HT-29 colon cancer cells are also shown (FIG. 4D).
Figure 4B:
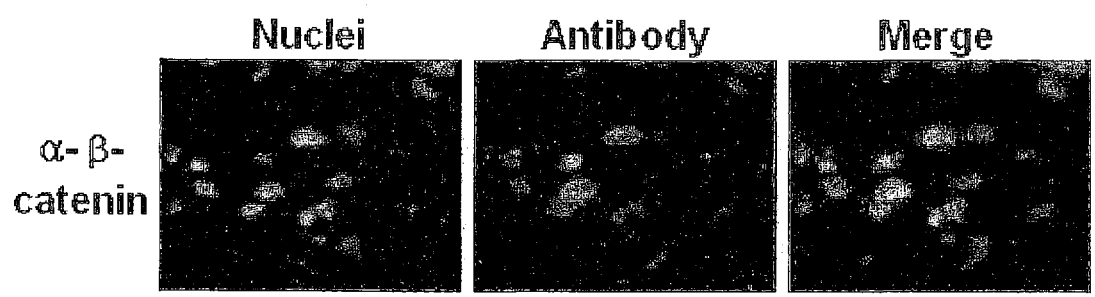
Figure 4C:
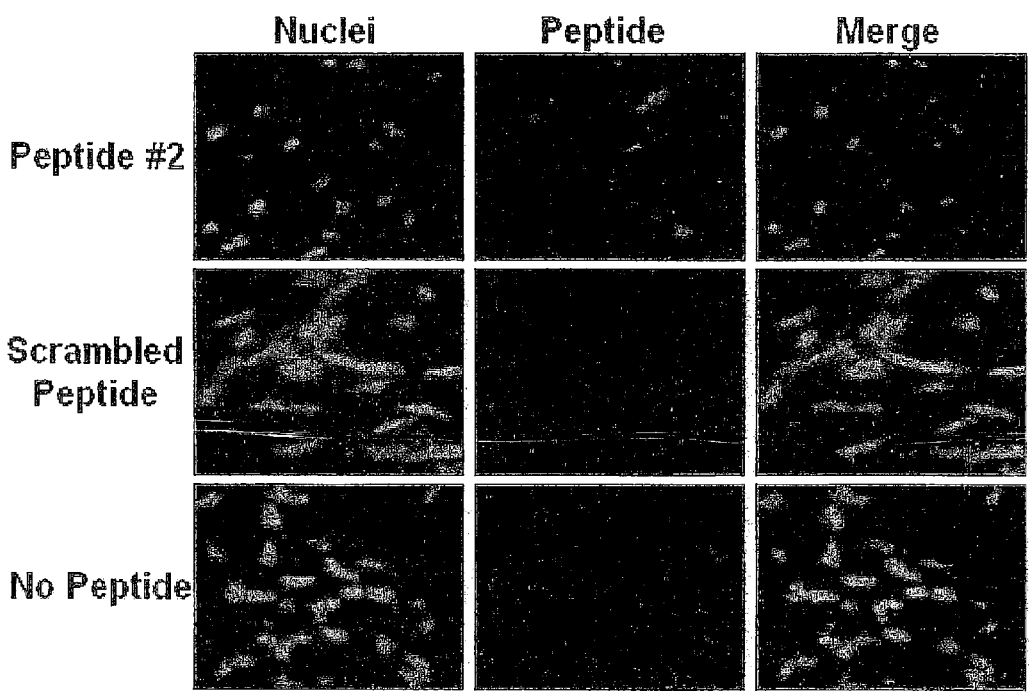
Figure 4D:
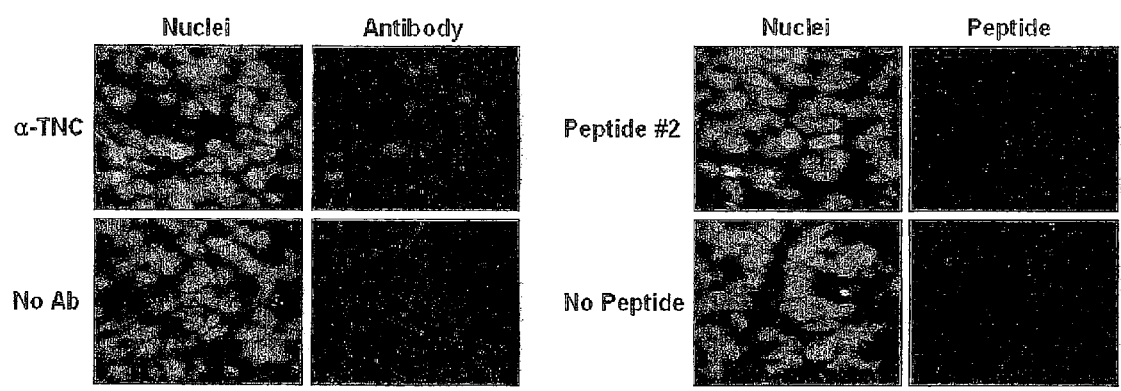
Figure 5A:
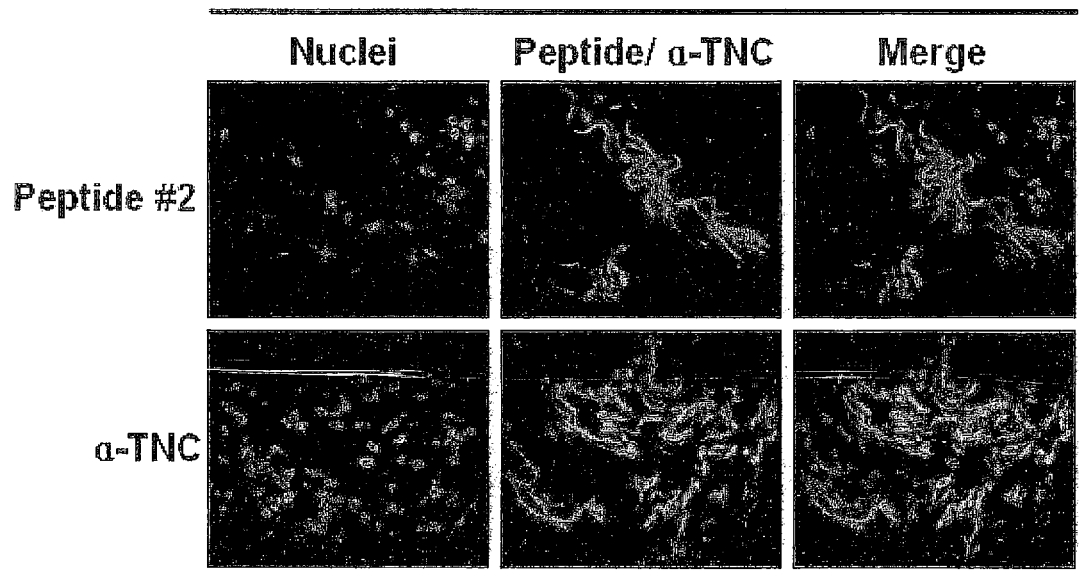
FIGS. 5A-5D represent detection for binding of peptide aptamer #2 to tumor patient lung tissue. Paraffin-embedded lung tissue from an adenocarcinoma (FIG. 5A), squamous cell carcinoma (FIG. 5B), bronchioloalveolar carcinoma (FIG. 5C) and normal (FIG. 5D) tissue was incubated at 4° C. for O/N with anti-tenascin C antibody (1:1000 dilution) or with biotin-labeled peptide aptamer #2 (10 μM). Tissues were counterstained with Hoechst33258. Magnification, ×630.
Figure 5B:
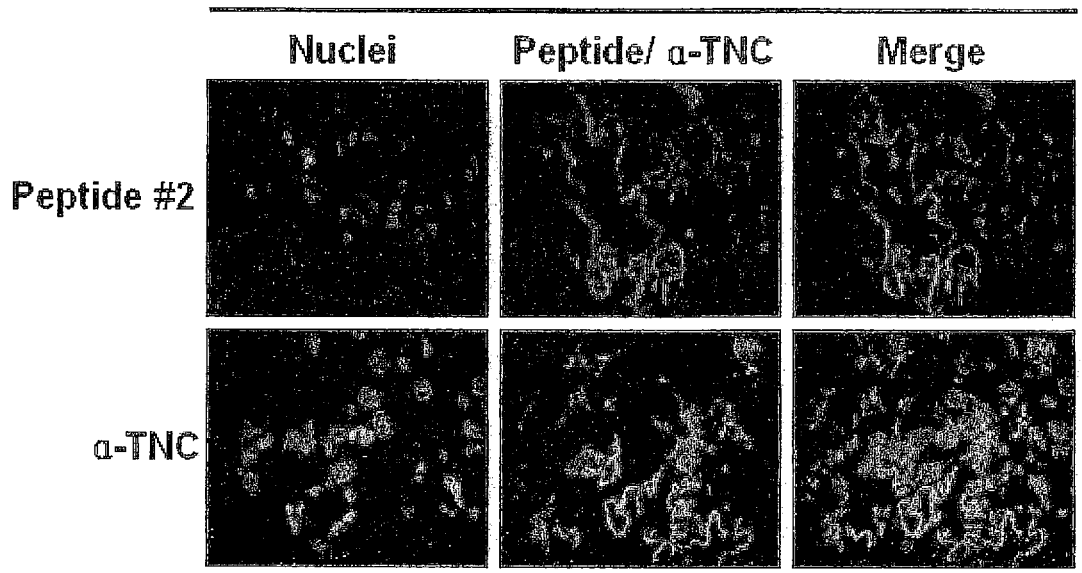
Figure 5C:
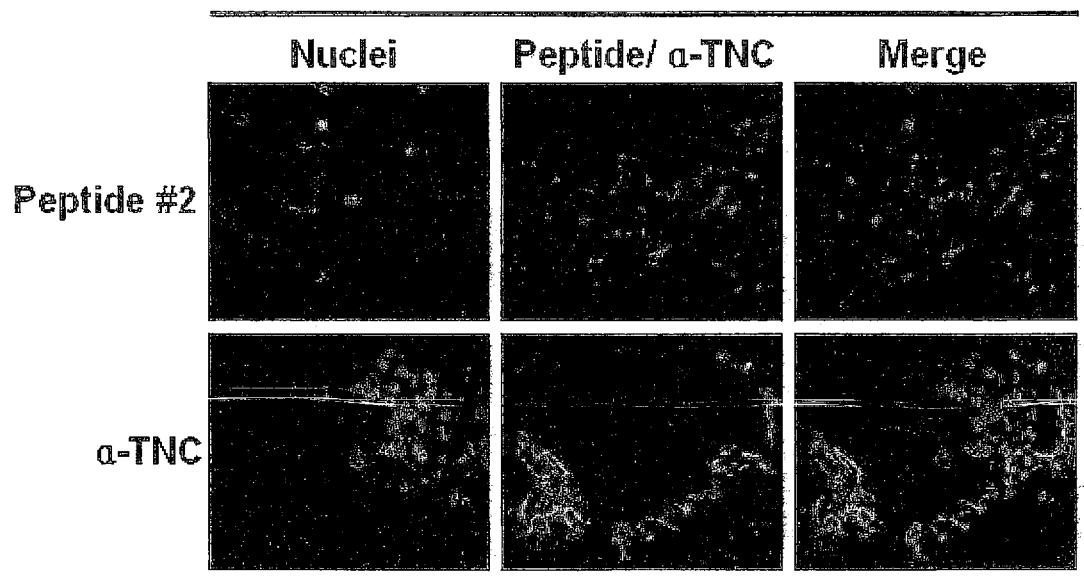
Figure 5D:
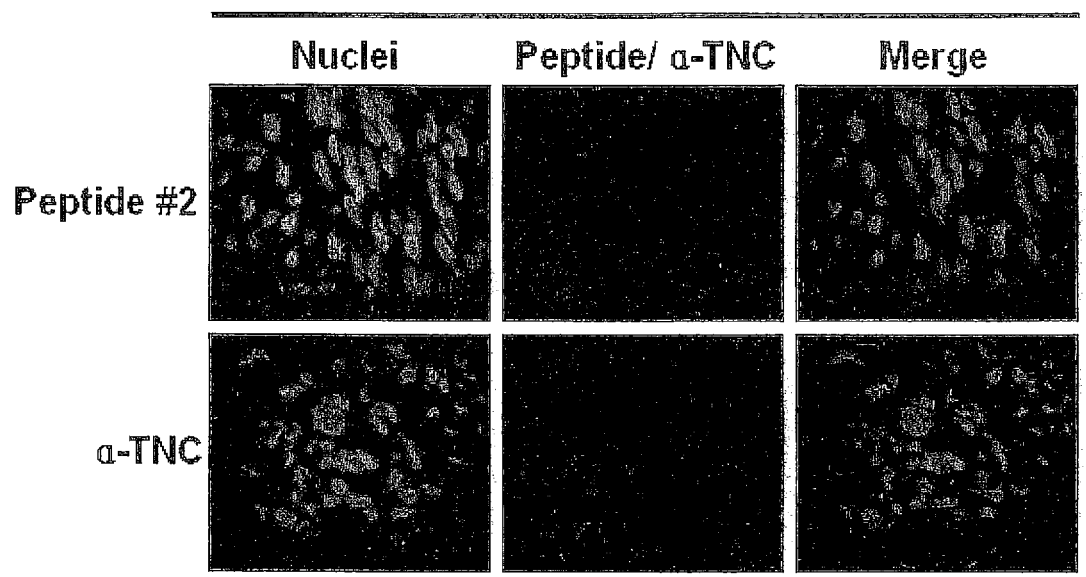

Even though the previous experiments suggest that aptamer #2 recognizes membrane-associated tenascin C in cultured cells, it was not clear whether it also bound to ECM-localized tenascin C in tumor tissues. The present inventors established a xenograft mouse model using U118MG glioblastoma cells, prepared tumor tissue sections and stained them with the anti-tenascin C antibody (FIG. 4A). Tenascin C protein signals appeared as strong spots or large blobs, mostly outside the nucleus, possibly in the ECM. We also used anti-β-catenin antibody to visualize the tumor cells in the sections (FIG. 4B). Interestingly, aptamer #2 gave the same prominent pattern of staining in the forms of spots and blobs (FIG. 4C). There was no significant staining when the peptide was omitted or the scrambled peptide aptamer #2 was used. The present inventors also developed a xenograft mouse model with HT-29 colon cancer cells, which do not express tenascin C and no aptamer signal was detected (FIG. 4D).

Detection of Tenascin C by Peptide Aptamer #2 in Tissue Microarrays

To see whether aptamer #2 also detected tenascin C in the tissues of cancer patients, the present inventors used a tissue microarray prepared with tissues from 52 lung cancer patients (36 adenocarcinomas, 15 squamous cell carcinomas and 1 bronchioloalveolar carcinoma) and 1 normal lung. With anti-tenascin C antibody we observed prominent expression of the protein, exclusively outside the cells, possibly in the ECM (FIG. 5). Streaks of expression were observed in every tumor tissue sample, especially strong in the adenocarcinomas and squamous cell carcinomas, with some spots in the bronchioloalveolar carcinoma. Such stromal bands may represent delineated packets of invasive tumor cells. The striking similarity of the staining patterns obtained with peptide aptamer #2 to those obtained with antibody demonstrate the specificity of the peptide aptamer. No peptide aptamer #2 staining was detected in normal tissue.

Modulation of Tenascin C-Induced Cell Rounding and Migration by the Peptide

Figure 6A:
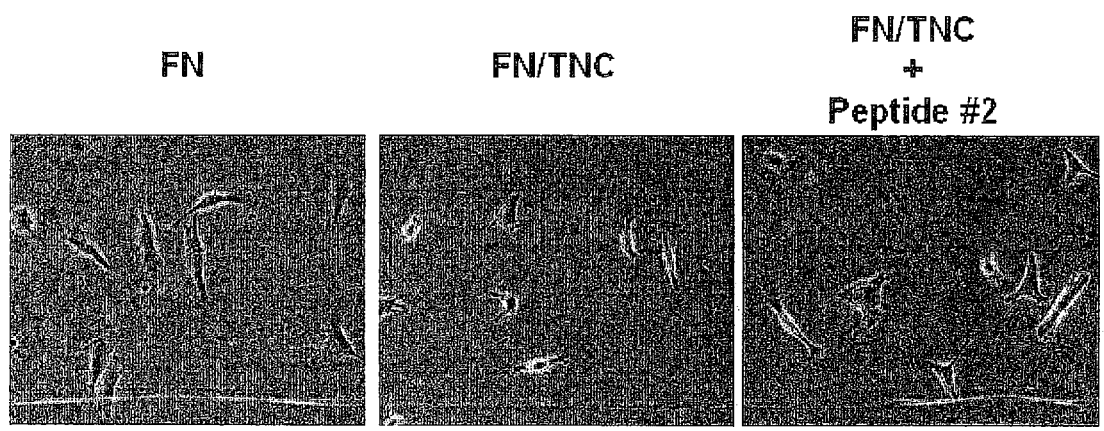
FIGS. 6A-6D represent reversion of tenascin-C-induced cell morphology and migration by the peptide aptamer.
Figure 6B:
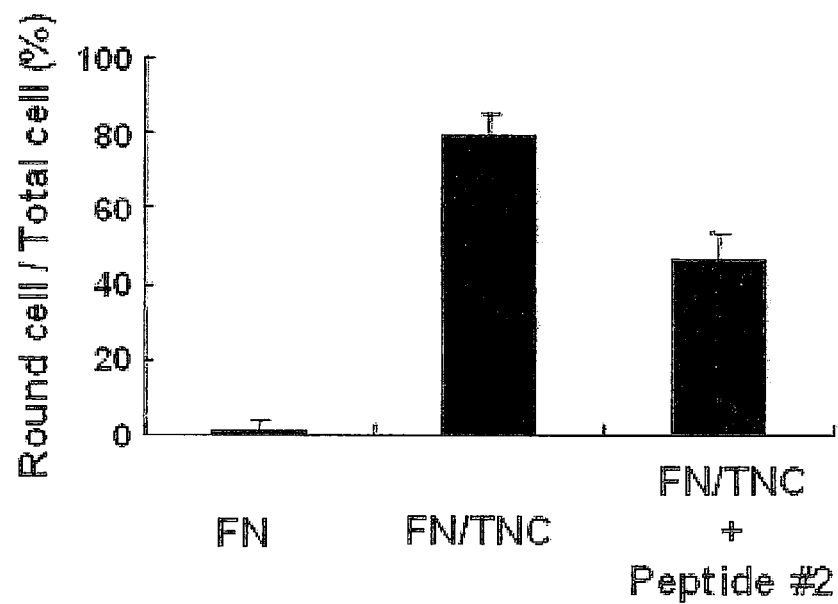
Figure 6C:
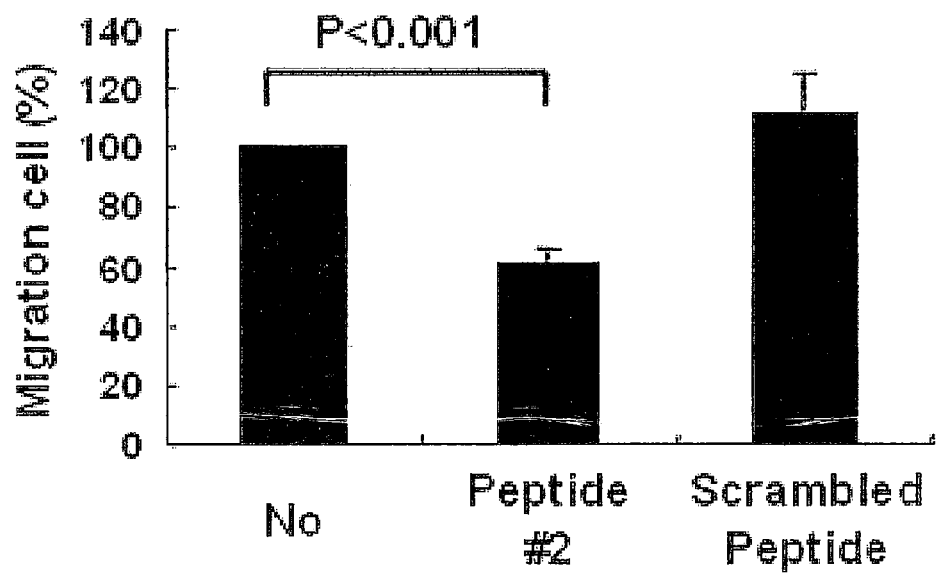
Figure 6D:
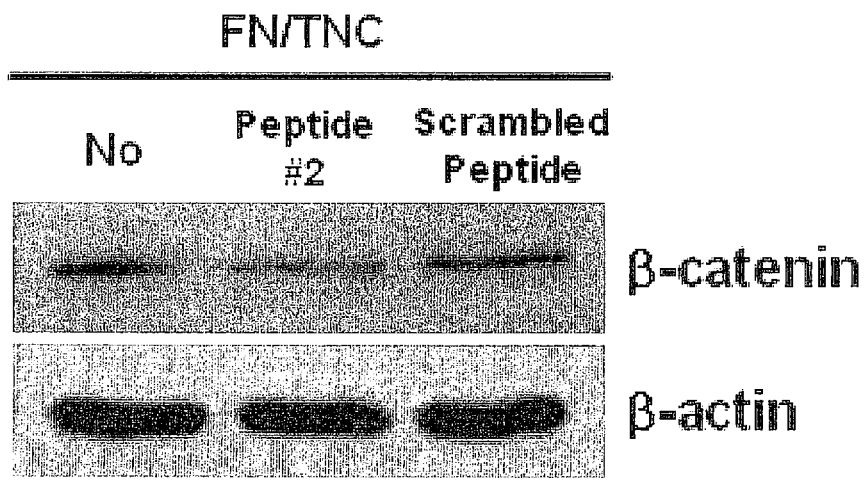

Tenascin C has anti-adhesive properties so it causes cells to become round and promotes migration. Thus the present inventors tested whether the peptide aptamer #2 inhibited tenascin C-induced cell rounding and migration in the cells. Globlastoma cells were plated on either the fibronectin or the fibronectin/tenascin C substratum and the cell morphologies were observed under microscopy. While most of the fibronectin plated cells had spread morphology, most of tenascin C plated cells had round morphology (FIGS. 6A and B). Notably, the present inventors observed significant reversion of tenascin C-induced rounding morphology by peptide aptamer #2. However, no significant change was induced by the scrambled peptide was used. The present inventors also tested the migratory potential of the glioblastoma cells in these conditions and found that tenascin C-induced cell migration was significantly reduced by the incubation of peptide aptamer #2. No significant reduction in cell migration was observed for the scrambled peptide (FIG. 6C). These results suggest that tenascin C-binding peptide #2 can modulates diverse oncogenic functions of tenascin C.

FURTHER DISCUSSION

The present inventors have shown here that the tenascin C binding peptide aptamer #2 can specifically recognize the expression of human tenascin C protein in xenograft mouse models as well as in human tumor patient tissues. Most significantly, the peptide aptamer #2 inhibited the tenascin C-induced cell rounding and migration which are the hallmarks of cancer cell metastasis. As far as the present inventors know, this is the first report on the selection of a tenascin C binding peptide aptamer, and also the first test of its utility as a diagnostic and therapeutic tool for tenascin C expressing solid tumors. To further enhance the value of the present study, it might be necessary to combine the peptide aptamer sequences to targeting and therapeutic agents and test its theragonostic utility in vivo.

Tenascin C is highly expressed in most solid tumors generally in the ECM or stromal cells surrounding tumor cells (23). Since the large isoform of tenascin C is overexpressed in lung cancers, quantitative as well as qualitative changes were observed (23, 24). Also immunohistochemical analysis of human lung tumor tissues has demonstrated localized tenascin staining in the focal areas of stroma, unlike the extensive expression of fibronectin and collagen type IV (25, 26). Here the present inventors could recapitulate the expression pattern of tenascin C in cultured cancer cells as well as in human cancer patient tissues with the peptide aptamer #2. Surprisingly, the interesting expression pattern of tenascin C, forming stromal bands delineating packets of invasive tumor cells, were also observed with the peptide aptamer #2 (see FIG. 5).

Roles of tenascin C in tumorigenesis and tumor metastasis have not yet been clearly understood. In contrast to most ECM proteins involved in substrate-cell adhesion, tenascin C has anti-adhesive properties, thus the overexpression of tenascin C in the focal regions of stroma may alter the adhesiveness of tumor cells to the ECM, and affect their invasiveness. In fact, tenascin C expression and matrix metalloproteinase activation seem to be associated in recurrent lung cancers (27) and in glioma cells (28). Moreover, tenascin C may also alter cancer cell signaling. For example, overexpression near the focal invasive point of a tumor could promote the survival and metastasis of the tumor cells. In fact, tenascin C has been reported to induce cell survival and proliferation signals involving the Akt as well as Wnt pathways, in various cells (29-32). Whatever the mechanism of tenascin C induced signaling, it clearly induces the rounding and mobilization of the cells in culture, which are critical for cancer cell metastasis (1-2, 4).

It is also possible that tenascin C promotes tumor metastasis by modulating the behavior of other cells in tumor tissues. Thus, overexpression of the large isoform of tenascin C inhibits the proliferation of infiltrating T-cells and downregulates the effector functions of lymphocytes in human lung cancer (24). In addition, tenascin C modulates recruitment of tumor stroma and macrophages, such that, in human atheosclerotic plaques, tenascin C expression is correlated with macrophage infiltration (33, 34). Tenascin C may activate angiogenesis by regulating the expression of Vascular Endothelial Growth Factor-A (35). Furthermore, tenascin C modulate the interaction between tumor cells and components of the ECM such as cell surface annexin II (36).

Due to its highly localized expression, tenascin C could be an extremely valuable target for tumor-specific targeting of therapeutic agents. For that reason, a tenascin C-specific monoclonal antibody is already in clinical trial (10-12, 37) and the refinement of monoclonal anti-tenascin C antibodies is under study (38). In addition, RNA aptamers have been developed for tumor imaging (13, 39). Considering the vast potential of peptides in cancer therapy (40), we hope to develop the peptide aptamer #2 as an exciting starting point for redesigning gene therapeutic viral vehicles for peptide-based tumor targeting (15-20, 41).

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Chiquet-Ehrismann R, Tucker R P. Connective tissues: signaling by tenascins. *Int J Biochem Cell Biol*, 36:1085-9(2004).
2. Chiquet-Ehrismann R. Tenascins. *Int J Biochem Cell Biol*, 36:986-90(2004).
3. Orend G. Potential oncogenic action of tenascin C in tumorigenesis. *Int J Biochem Cell Biol*, 37:1066-83(2005).
4. Orend G, Chiquet-Ehrismann R. Tenascin C induced signaling in cancer. *Cancer Lett*, 244:143-63(2006).
5. Hsia H C, Schwarzbauer J E. Meet the tenascins: Multifunctional and mysterious. *J Biol Chem*, 280:26641-4 (2005).
6. Adams M, Jones J L, Walker R A, et al. Changes in tenascin C isoform expression in invasive and preinvasive breast disease. *Cancer Res*, 62:3289-97(2002).
7. Juuti A, Nordling S, Louhimo J, et al. Tenascin C expression is upregulated in pancreatic cancer and correlates with differentiation. *J Clin Patho*, 57:1151-5(2004).
8. Berndt A, Anger K, Richter P, et al. Differential expression of tenascin C splicing domains in urothelial carcinomas of the urinary bladder. *J Cancer Res Clin Oncol*, 132:537-46 (2006).
9. Takeda A, Otani Y, Iseki H, et al. Clinical significance of large tenascin C spliced variant as a potential biomarker for colorectal cancer. *World J Surg*, 31:388-94(2007).
10. Brack S S, Silacci M, Birchler M, Neri D. Tumor-targeting properties of novel antibodies specific to the large isoform of tenascin C. *Clin Cancer Res*, 12:3200-8(2006).
11. Akabani G, Reardon D A, Coleman R E, et al. Dosimetry and radiographic analysis of 131I-labeled anti-tenascin 81C6 murine monoclonal antibody in newly diagnosed patients with malignant gliomas: a phase II study. *J Nucl Med*, 46:1042-51(2005).
12. Silacci M, Brack S S, Spath N, et al. Human monoclonal antibodies to domain C of tenascin C selectively target solid tumors in vivo. *Protein Eng Des Sel*, 19:471-8(2006).
13. Hicke B J, Marion C, Chang Y F, et al. Tenascin Captamers are generated using tumor cells and purified protein. *J Biol Chem*, 276:48644-54(2001).
14. Hicke B J, Stephens A W, Gould T, et al. Tumor targeting by an aptamer. *J Nucl Med*, 47:668-78(2006).
15. Rasmussen U B, Schreiber V, Schultz H, et al. Tumor cell-targeting by phage-displayed peptides. *Cancer Gene Ther;* 9:606-12(2002).
16. Lee S M, Lee E J, Hong H Y, et al. Targeting bladder tumor cells in vivo and in the urine with a peptide identified by phage display. *Mol Cancer Res*, 5:11-9(2007).
17. Aggarwal S, Singh P, Topaloglu O, et al. A dimeric peptide that binds selectively to prostate-specific membrane antigen and inhibits its enzymatic activity. *Cancer Res*, 66:9171-7(2006).
18. Jager S, Jahnke A, Wilmes T, et al. Leukemia targeting ligands isolated from phage display peptide libraries. *Leukemia*, 21:411-20(2007).
19. Grifman M, Trepel M, Speece P, et al. Incorporation of tumor-targeting peptides into recombinant adeno-associated virus capsids. *Mol Ther;* 3:964-75(2001).
20. White S J, Nicklin S A, Buning H, et al. Targeted gene delivery to vascular tissue in vivo by tropism-modified adeno-assocoated virus vectors. *Circulation*, 109:513-9 (2004).
21. Hajitou A, Pasqualini R, Arap W. Vascular targeting: Recent advances and therapeutic perspectives. *Trends Cardiovasc Med*, 16:80-8(2006).
22. Marchler-Bauer A, Anderson J B, Derbyshire M K, et al. CDD: a conserved domain database for interactive domain family analysis. *Nucleic Acids Res*, 35:D237-40(2007).
23. Oyama F, Hirohashi S, Shimosato Y, et al. Qualitative and quantitative changes of human tenascin expression in transformed lung fibroblast and lung tumor tissues: comparison with fibronectin. *Cancer Res*, 51:4876-81(1991).
24. Parekh K, Ramachandran S, Cooper J, et al. Tenascin C, over expressed in lung cancer down regulates effector functions of tumor infiltrating lymphocytes. *Lung Cancer;* 47:17-29(2005).
25. Sethi T, Rintoul R C, Moore S M, et al. Extracellular matrix proteins protect small cell lung cancer cells against apoptosis: a mechanism for small cell lung cancer growth and drug resistance in vivo. *Nat Med*, 5:662-8(1999).
26. Han J Y, Kim H S, Lee S H, et al. Immunohistochemical expression of integrins and extracellular matrix proteins in non-small cell lung cancer: correlation with lymph node metastasis. *Lung Cancer;* 41:65-70(2003).
27. Cai M, Onoda K, Takao M, et al. Degradation of tenascin C and activity of matrix metalloproteinase-2 are associated with tumor recurrence in early stage non-small cell lung cancer. *Clin Cancer Res*, 8:1152-6(2002).
28. Sarkar S, Nuttall R K, Liu S, et al. Tenascin C stimulates glioma cell invasion through matrix metalloproteinase-12. *Cancer Res*, 66:11771-80(2006).
29. Jang J H, Chung C P. Tenascin C promotes cell survival by activation of Akt in human chondrosarcoma cell. *Cancer Lett*, 229:101-5(2005).

30. Kakinuma Y, Saito F, Osawa S, Miura M. A mechanism of impaired mobility of oligodendrocyte progenitor cells by tenascin C through modification of wnt signaling. *FEBS Lett*, 568:60-4(2004).
31. Beiter K, Hiendlmeyer E, Brabletz T, et al. 3-Catenin regulates the expression of tenascin C in human colorectal tumors. *Oncogene*, 24:8200-4(2005).
32. Ruiz C, Huang W, Hegi M E, et al. Differential gene expression analysis reveals activation of growth promoting signaling pathways by tenascin C. *Cancer Res*, 64:7377-85(2004).
33. Talts J F, Wirl G, Dictor M, et al. Tenascin C modulates tumor stroma and monocyte/macrophage recruitment but not tumor growth or metastasis in a mouse strain with spontaneous mammary cancer. *J Cell Sci*, 112:1855-64 (1999).
34. Wallner K, Li C, Shah P K, et al. Tenascin C is expressed in macrophage-rich human coronary atherosclerotic plaque. *Circulation*, 99:1284-9(1999).
35. Tanaka K, Hiraiwa N, Hashimoto H, et al. Tenascin C regulates angiogenesis in tumor through the regulation of vascular endothelial growth factor expression. *Int J Cancer;* 108:31-40(2004).
36. Esposito I, Penzel R, Chaib-Harrireche M, et al. Tenascin C and annexin II expression in the process of pancreatic carcinogenesis. *J Pathol*, 208:673-85(2006).
37. Reardon D A, Akabani G, Coleman R E, et al. Phase II trial of murine 131I-labeled antitenascin monoclonal antibody 8106 administered into surgically created resection cavities of patients with newly diagnosed malignant gliomas. *J Clin Oncol*, 20:1389-97(2002).
38. Bellofiore P, Petronzelli F, De Martino T, et al. Identification and refinement of a peptide affinity ligand with unique specificity for a monoclonal anti-tenascin C antibody by screening of a phage display library. *J Chromatogr A*, 1107:182-91(2006).
39. Daniels D A, Chen H, Hicke B J, et al. A tenascin C aptamer identified by tumor cell SELEX: systematic evolution of ligands by exponential enrichment. *Proc Natl Acad Sci USA*, 100:15416-21(2003).
40. Khandare J J, Minko T. Antibodies and peptides in cancer therapy. *Crit Rev Ther Drug Carrier Syst*, 23:401-35 (2006).
41. Work L M, Büning H, Hunt E, et al. Vascular bed-targeted in vivo gene delivery using tropism-modified adeno-associated viruses. *Mol Ther;* 13:683-93(2006).

What is claimed is:

1. A method for detecting the level of tenascin C comprising:
   (a) providing a biological tissue derived from a subject;
   (b) contacting an anti-tenascin C peptide aptamer to the biological tissue, wherein the peptide aptamer comprises the amino acid sequence of SEQ ID NO:2, and wherein the peptide aptamer is attached to a substance that generates a detectable signal; and
   (c) analyzing the level of a complex of the tenascin C and the peptide aptamer in the biological tissue.

2. The method according to claim 1, wherein the peptide aptamer further comprises 2-4 Gly residues in its N-terminal.

3. A method for screening for the presence of a tumor in a biological tissue, wherein the tumor is characterized by the expression of tenascin C, and wherein the tumor is stomach cancer, lung cancer, breast cancer, ovarian cancer, liver cancer, bronchogenic cancer, pancreatic cancer, colon cancer, brain cancer, or prostate cancer, comprising:
   (a) providing the biological tissue derived from a subject;
   (b) contacting an anti-tenascin C peptide aptamer to the biological tissue, wherein the peptide aptamer comprises the amino acid sequence of SEQ ID NO:2, and wherein the peptide aptamer is attached to a substance that generates a detectable signal; and
   (c) analyzing the level of a complex of the tenascin C and the peptide aptamer in the biological tissue, wherein an increased level of the complex of the tenascin C and the peptide aptamer compared to a control tissue from a normal subject indicates that the subject has the tumor.

4. The method according to claim 3, wherein the tumor is glioblastoma, colon adenocarcinoma or lung carcinoma.

5. The method according to claim 3, wherein the peptide aptamer further comprises 2-4 Gly residues in its N-terminal.

* * * * *